US006979350B2

(12) United States Patent
Moll et al.

(10) Patent No.: US 6,979,350 B2
(45) Date of Patent: Dec. 27, 2005

(54) METHODS FOR REGULATING THE FLOW OF BLOOD THROUGH THE BLOOD SYSTEM

(75) Inventors: Franciscus Laurens Moll, La Bosch en Duin (NL); Menno Kalmann, Elsp-eet (NL)

(73) Assignee: 3F Therapeutics, Inc., Lake Forest, CA (US)

( * ) Notice: Subject to any disclaimer, the term of this patent is extended or adjusted under 35 U.S.C. 154(b) by 0 days.

(21) Appl. No.: 10/619,725

(22) Filed: Jul. 15, 2003

(65) Prior Publication Data

US 2004/0015230 A1   Jan. 22, 2004

Related U.S. Application Data

(63) Continuation of application No. 09/630,403, filed on Aug. 1, 2000, now Pat. No. 6,605,112, which is a continuation of application No. 08/992,350, filed on Dec. 17, 1997, now Pat. No. 6,287,334.

(30) Foreign Application Priority Data

Dec. 18, 1996   (NL) .................................... 1004827

(51) Int. Cl.$^7$ ............................................... A61F 2/24
(52) U.S. Cl. .................... 623/1.24; 623/2.17; 623/23.7; 623/900
(58) Field of Search ............................ 623/1.24, 1.26, 623/2.12–2.19, 23.68, 23.7, 900

(56) References Cited

U.S. PATENT DOCUMENTS

| 3,657,744 A | 4/1972 | Ersek |
| 3,671,979 A | 6/1972 | Moulopoulos |
| 4,291,420 A | 9/1981 | Reul |
| 4,297,749 A | 11/1981 | Davis et al. |
| 4,470,157 A | 9/1984 | Love |
| 4,787,901 A | 11/1988 | Baykut |
| 4,994,077 A | 2/1991 | Dobben |
| 5,141,491 A | 8/1992 | Bowald |
| 5,327,774 A | 7/1994 | Nguyen et al. |
| 5,332,402 A | 7/1994 | Teitelbaum |
| 5,411,552 A | 5/1995 | Andersen et al. |
| 5,480,423 A | 1/1996 | Ravenscroft et al. |
| 5,500,014 A | 3/1996 | Quijano et al. |
| 5,607,465 A | 3/1997 | Camilli |
| 5,713,953 A | 2/1998 | Vallana et al. |
| 5,735,859 A | 4/1998 | Fischell et al. |
| 5,741,326 A | 4/1998 | Solovay |
| 5,741,333 A | 4/1998 | Frid |

(Continued)

FOREIGN PATENT DOCUMENTS

| DE | 1932817 | 1/1970 |
| DE | 19532846 | 3/1997 |

(Continued)

*Primary Examiner*—David H. Willse
*Assistant Examiner*—Javier G. Blanco
(74) *Attorney, Agent, or Firm*—Jones Day

(57) ABSTRACT

A valve prosthesis is disclosed which is implantable within a vein or other blood vessel of a patient using a minimally-invasive surgical procedure. The prosthesis includes a tubular wire frame which presses radially outward against the inner walls of the blood vessel following implantation to hold the prosthesis in position. Multiple flow-resistive pockets that open and close in response to changes in blood flow direction are attached to the frame to impede the flow of blood in the reverse direction. The prosthesis is implanted using an introducer catheter which holds the prosthesis in a radially-compressed state as the prosthesis is inserted into and positioned within the blood vessel.

3 Claims, 3 Drawing Sheets

U.S. PATENT DOCUMENTS

| | | |
|---|---|---|
| 5,800,506 A | 9/1998 | Perouse |
| 5,824,061 A | 10/1998 | Quijano et al. |
| 5,855,601 A | 1/1999 | Bessler et al. |
| 5,957,949 A | 9/1999 | Leonhardt et al. |
| 6,027,525 A | 2/2000 | Suh et al. |
| 6,110,201 A | 8/2000 | Quijano et al. |
| 6,200,336 B1 | 3/2001 | Pavcnik et al. |
| 6,241,763 B1 | 6/2001 | Drasler et al. |
| 6,299,637 B1 | 10/2001 | Shaolian et al. |
| 6,315,793 B1 | 11/2001 | Bokros et al. |
| 2001/0010017 A1 | 7/2001 | Letac et al. |

FOREIGN PATENT DOCUMENTS

| | | |
|---|---|---|
| EP | 0 155 245 | 3/1985 |
| EP | 0667133 | 8/1995 |
| GB | 1477643 | 6/1977 |
| GB | 2 056 023 | 3/1981 |
| RU | 1271508 | 11/1986 |
| WO | WO 9619159 | 6/1996 |

METHODS FOR REGULATING THE FLOW OF BLOOD THROUGH THE BLOOD SYSTEM

This application is a continuation of U.S. application Ser. No. 09/630,403, filed Aug. 1, 2000 (issued as U.S. Pat. No. 6,605,112), which is a continuation of U.S. application Ser. No. 08/992,350 (issued as U.S. Pat. No. 6,287,334), filed on Dec. 17, 1997, which claims priority from Netherlands Application No. 1004827, filed Dec. 18, 1996, each of the aforementioned applications being incorporated by reference in their entirety.

The present invention relates to a device for regulating the flow of blood in blood vessels.

The blood system, and in particular the venal blood system of the legs and arms are provided with valves, at predetermined positions, which ensure that blood cannot flow back along the system in the direction from which it has just been pumped, to only be displaced in the direction of the heart.

In the arms and legs, there is a deep and a surface venal system.

Due to various causes, thrombosis can occur in especially the deep venal system. Following thinning of the blood, passage of the blood through the system is often again possible, but in this case the valves do not effectively close off the system and often leak. This causes an increased venal blood pressure in the direction of the ankles, which leads to many problems, such as varicose veins and the infamous "open leg". This type of complaint is wide spread among people who spend a vast majority of their working hours in a standing position, for instance surgeons.

The surface venal system of the leg is weaker than the deep system, and has the tendency to spontaneously widen, whereby the valves no longer function effectively, leading to varicose veins, which, apart from being highly unattractive, are also very painful. Major surgery is often required to deal with these blood vessel valve problems.

For example varicose veins are presently surgically operated on, by either closing off the vein, which leads to a reduced blood flow capacity and extra pressure on surrounding blood vessels in order to ensure blood supply, or by completely removing the varicose veins, which leads to the same problem.

An object of the present invention is to obviate one or more of these problems.

According to a first aspect, the present invention provides a device for regulating the flow of blood in blood vessels, comprising one or more flow stoppage elements, each comprising:
 a flareable proximal end, flareable between a flared, flow stoppage configuration and a substantially flattened, flow permitting configuration, and
 a middle section extending from the proximal end to terminate in a distal end.

By introducing a synthetic device which acts as a valve, the blood flow is now able to be regulated in substantially the normal manner.

The device preferably further comprises:
 an opening associated with the proximal end, the middle section comprising one or more sidewalls extending from this proximal end opening to join together at the distal end, the sidewalls being displaceable, by the flow of blood through the device between the flared configuration, wherein the element encloses a temporary blood storage area, and the substantially flattened configuration wherein the one or more sidewalls lie substantially flat adjacent to each other.

When occupying the blood flow stoppage configuration, the flow stoppage element encloses a temporary blood storage area between its open proximal end and the closed distal end. In this way between heartbeats, which force the blood through the venal system, any blood flowing in the opposite direction to the blood stream opens the proximal end of the stoppage element thereby forcing the sidewalls apart to enter the temporary blood storage area, instead of passing through the device to leak back into the blood vessel in the direction from where it has just been pumped. Since opening of the blood flow stoppage element effectively closes off the blood vessel, a very effective valve is provided.

The flow stoppage element is preferably mounted on a support having such a form as to pass within a blood vessel. This provides extra stability.

Further, the support frame comprises a resilient wire and is biased toward an unrolled configuration.

The stoppage element is preferably substantially conical in shape when occupying the blood flow stoppage configuration, the closed distal end being synonymous with the tip of the cone and the proximal end opening being synonymous with the flared base of the cone. This yields a highly effective valve working.

The support is preferably adjustable between an introducing form, wherein the device is suitable for introducing into a blood vessel, and an expanded form suitable for supporting the stoppage element within a blood vessel at the desired working location thereof, and most preferably has such a form as to have substantially the same length when occupying its introducing form as when occupying its expanded form. Accordingly the device can be effectively introduced to a pre-desired location within a blood vessel, whereafter it is expandable to take up its working form. Since the support has substantially the same length when in its introducing form as in its expanded form, the stoppage elements remain effectively supported, and any damage ensuing from alteration of the length of the support within the blood system is effectively obviated.

In order to yield a very effective valve working, the support preferably comprises substantially separate frame sections for each of the one or more fluid passage stoppage elements.

According to another aspect of the present invention, there is provided a support for a fluid stoppage element as referred to above.

According to yet a further aspect of the present invention there is provided a method for regulating the flow of blood in the blood stream comprising introducing the above device into a blood vessel, so that the distal end thereof is arranged downstream from the proximal end, wherein the proximal end opening is closed by the pressure of blood flowing through the device, as blood is pumped through the system by the heart, wherein blood flowing in the opposite direction to which it is pumped between beats, flows into the proximal end of the device, which is subsequently thereby opened to force the sidewalls of the device against the blood vessel walls, thereby closing off the passage of blood in the blood vessel, wherein blood is trapped in the temporary blood storage area enclosed by the sidewalls of the device before a subsequent volume of blood being pumped through the device claps said sidewalls shut, thereby expelling blood out of the temporary storage area and further through the system.

The introducer preferably comprises an elongated sliding member which is advanceable by a physician to forcibly displace the valve prosthesis from the hollow distal portion of said introducer into the blood vessel.

The present invention will now be further clarified by way of the following specific description, which refers to FIGS. 1 to 7, wherein.

A device 1 (FIG. 1) according to the present invention has a proximal end 2 and a distal end 4.

Figure 2:
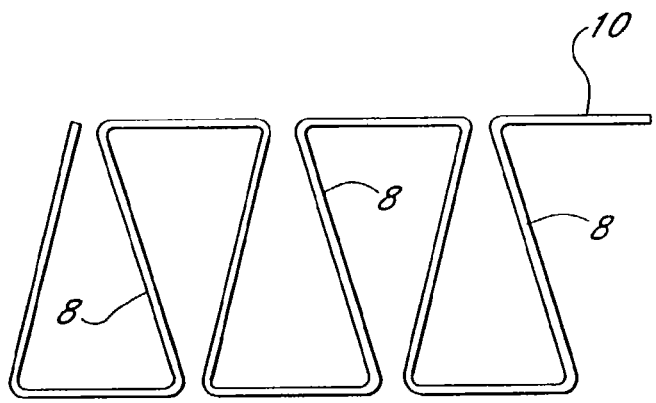
FIG. 2 is a side view of a support for a flow stoppage element according to the present invention.

Blood flow stoppage elements 6, having the form of flexible hollow cones, are each supported on a substantially triangular frame section 8 of a support 10, see also FIG. 2.

The valve elements 6 have an inner wall 12 and an outer wall 14 extending from a proximal end (2) opening 16 in the "flared" configuration to join together and terminate in the form of a pointed end section 17 at the distal end 4.

Figure 1:
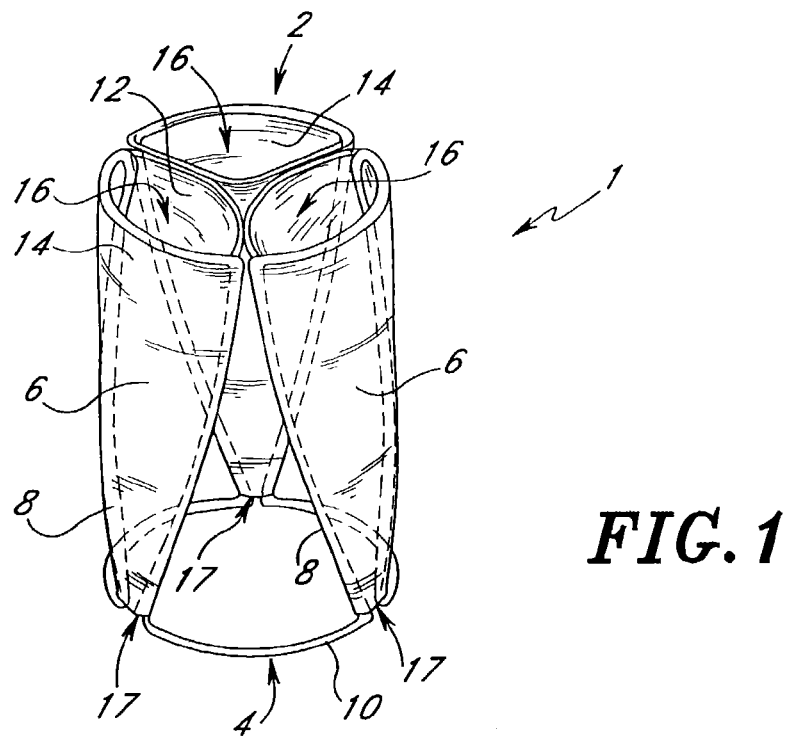
FIG. 1 is a perspective view of the device according to the present invention.

The support 10 is preferably made of a continuous length of memory metal, having, as shown in FIGS. 1 and 2, three substantially separate frame sections 8 for supporting each valve element 6.

Figure 3:
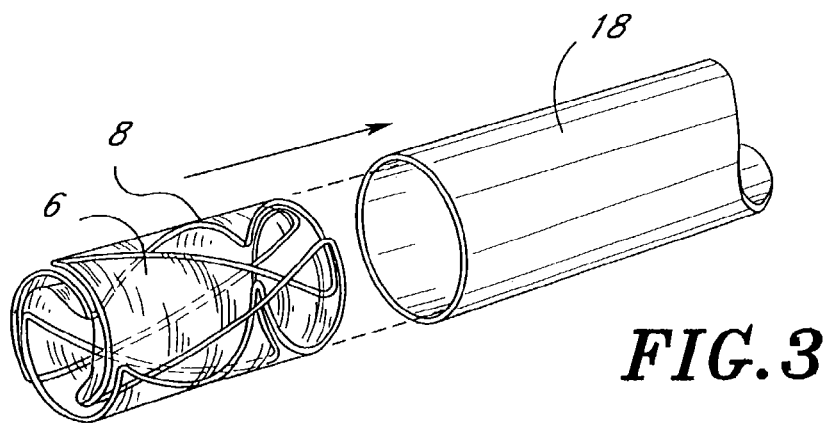
FIG. 3 is a perspective view of the device from FIG. 1, when occupying its introducing form, as to be introducible into a blood vessel.

As shown in FIG. 3, the frame 10 can be rolled up so that frame sections 8 partially overlap one another.

In such a position the device 1 is easily introduced into a blood vessel.

On being placed at its desired position within the blood system, the device, once the memory metal has achieved a particular predetermined temperature, will expand in order to assume its working form as shown in FIG. 1, whereby since in its introducing form (FIG. 3), an area of overlap exists between the terminal frame sections 8, the device 1 remains substantially the same length in its working position (FIG. 1) as in it introducing position (FIG. 3).

In order to ensure biocompatibility, the support and blood stoppage elements are made of biocompatible material, whereby the blood stoppage elements are most preferably made of polytetrafluoroethylene (PTFE).

Figure 4:
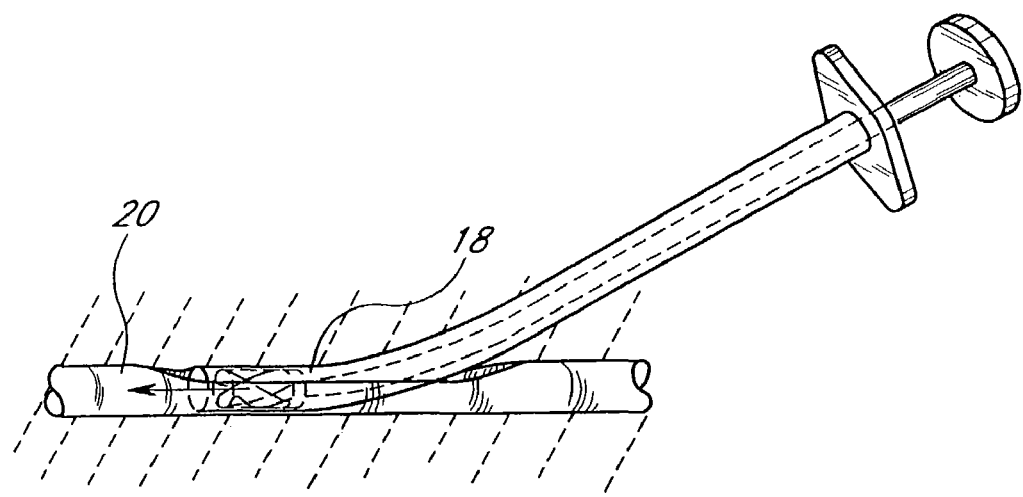
FIG. 4 is a perspective view showing the introduction of a device as shown in FIG. 1 into a blood vessel.
Figure 7:
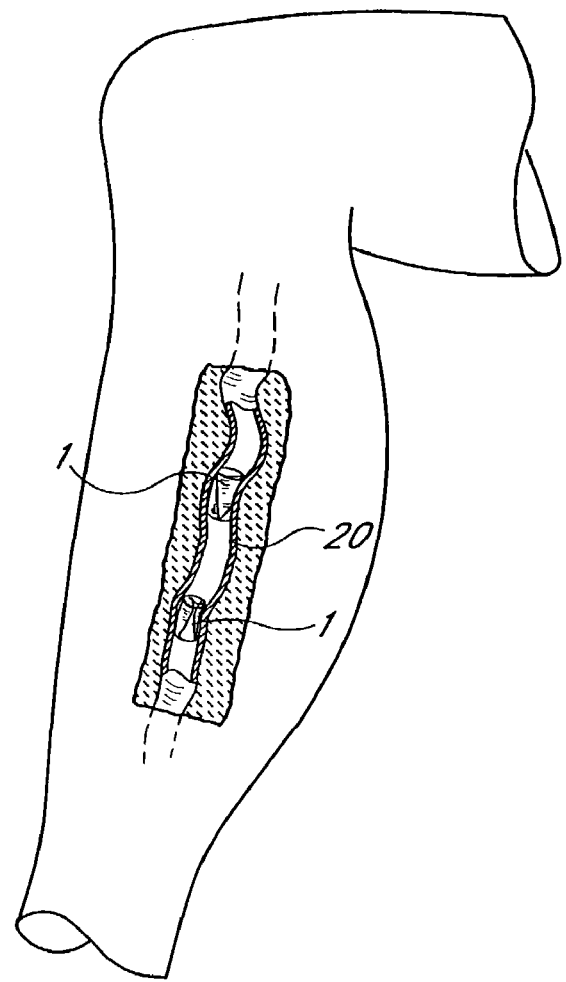
FIG. 7 is a perspective view of two devices as shown in FIG. 1, when placed in a vein in the leg.

The device 1 is folded up into its introducing form, as shown in FIG. 3, whereafter once arranged in an introducing device 18, as shown in FIGS. 3 and 4, the device 1 is introducible into a blood vessel 20 as shown in FIG. 4.

On assuming its working configuration as shown in FIGS. 1, 5, 6 and 7, the blood is regulated in the blood vessel by the device as follows.

Blood is pumped through the blood vessel 20 (FIG. 5) and through the device 1 (FIG. 5) on the beat of the heart. This means that instead of flowing at a constant rate through the blood vessel, that blood flows through the blood system, in particular through veins, as a series of pulses. Between each pulse, the blood is not being actively forced through the system and can flow back from where it came.

Figures 5, 6:
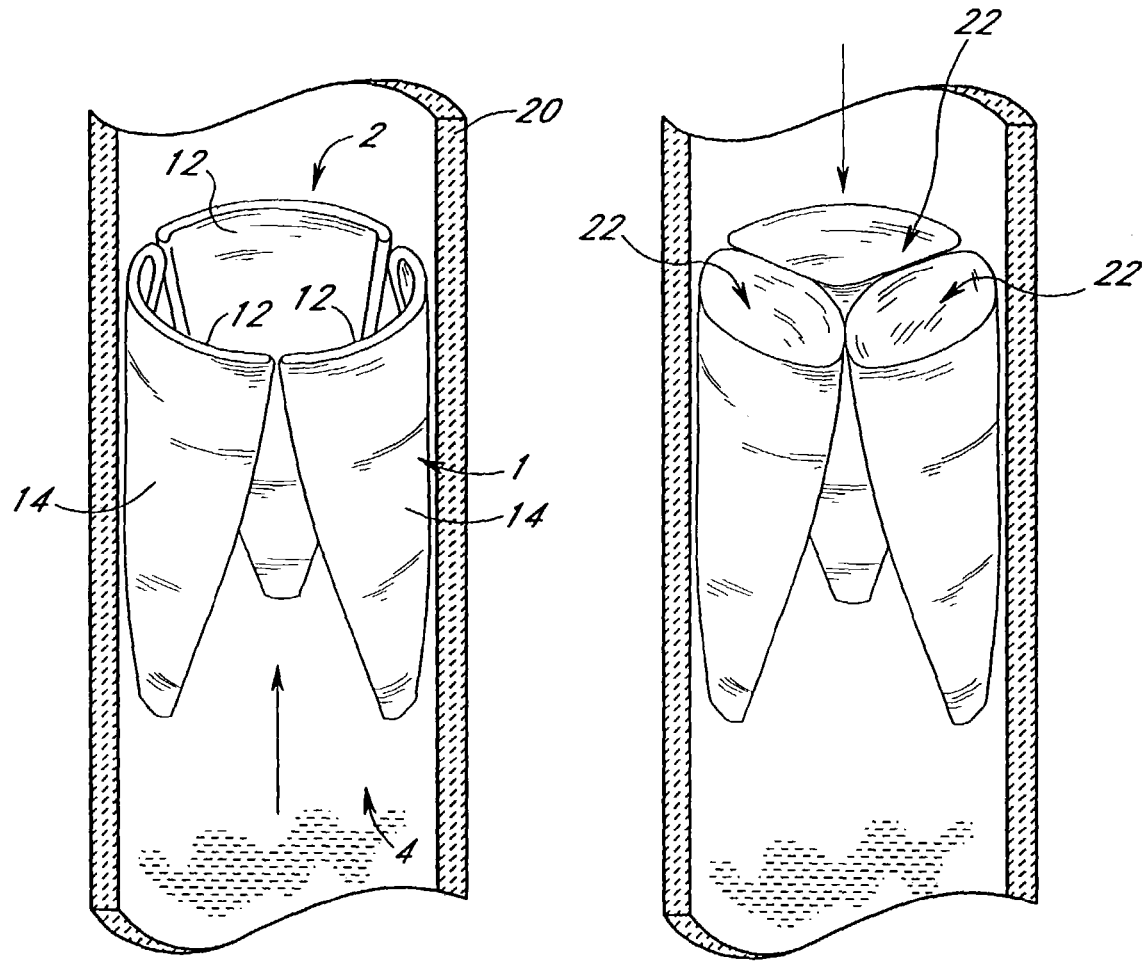
FIG. 5 is a perspective view as in FIG. 4, showing the device when occupying its blood flow through put position.
FIG. 6 shows the device from FIG. 1, with the support (not shown) in order to provide maximum clarity, when occupying its blood flow stoppage position within a blood vessel.

When actively pumped through the system, blood is forced through the device 1 through the distal end 4 and out of the proximal end 2 (FIG. 5).

In this position (FIG. 5), the flow of the blood through the device 1, forces the inner walls 12 of the stoppage elements 6 against the outer walls 14 thereof in order to effect a blood flow through channel.

Between heartbeats, blood having just passed through the proximal opening 2 of the device 1, can flow back down the blood vessel 20. On doing so, it forces the inner walls 12 away from the outer walls 14 of these elements 6 at the proximal end 2 of the device 1 to create the opening 16 leading into a temporary blood storage area 22. Since the inner walls 12 and the outer walls 14 are joined together at the distal end 4 of the device, the temporary blood storage area 22 is effected in each blood stoppage element 6 at this phase (FIG. 6).

During the next pulse of blood through the device 1 from the distal end 4, the inner walls 12 are forced against the outer walls 14 of the stoppage elements 6, thus forcing the blood temporarily stored therein out of the blood stoppage elements 6 and effecting the open channel to enable blood through flow.

What is claimed is:

1. A minimally invasive method of implanting a valve prosthesis device comprising a plurality of flexible, conical blood flow stoppage elements, each having a memory metal frame within an existing vein of a human to restore venous valvular function within the vein, the plurality of flexible, conical blood flow stoppage elements, each having a memory metal frame adapted to press outward against the inner walls of the vein to hold the plurality of flexible, conical blood flow stoppage elements, each having a memory metal frame in position within the vein following implantation, the method comprising the steps of:

collapsing the flexible, conical blood flow stoppage elements;

overlapping flareable proximal ends of the flexible, conical blood flow stoppage elements;

positioning the collapsed plurality of flexible, conical blood flow stoppage elements, each having a memory metal frame within a hollow distal portion of an introducer with the plurality of flexible, conical blood flow stoppage elements, each having a memory metal frame in a compressed state;

advancing the hollow distal portion of the introducer, with the plurality of flexible, conical blood flow stoppage elements, each having a memory metal frame positioned therein, into the vein of the human through an opening in a wall of the vein;

expelling the plurality of flexible, conical blood flow stoppage elements, each having a memory metal frame from the hollow distal portion of the introducer into the vein; and temperature expanding the plurality of flexible, conical blood flow stoppage element frames, and thereby expanding the flareable proximal ends of the blow flow stoppage elements such that they no longer overlap as so to expand to an operational state in which the plurality of flexible, conical blood flow stoppage elements, each having a memory metal frame are maintained in position within the vein by pressing outward against the inner walls of the vein.

2. The method of claim 1, wherein the step of expelling comprises slidably advancing an expulsion member distally within the introducer to forcibly displace the plurality of flexible, conical blood flow stoppage elements, each having a memory metal frame from the hollow distal portion of the introducer.

3. The method of claim 1, wherein the plurality of flexible, conical blood flow stoppage elements and memory metal frames is rollable upon itself to place the frames in a tubular configuration, and wherein the step of positioning comprises rolling the frames against a biasing force to place the plurality of flexible, conical blood flow stoppage elements and memory metal frames in a radially-compressed configuration that corresponds to an inner diameter of the hollow distal portion of the introducer.

* * * * *